(12) United States Patent
Ono et al.

(10) Patent No.: US 9,609,884 B2
(45) Date of Patent: *Apr. 4, 2017

(54) ANTI-FATIGUE AGENT

(75) Inventors: Yoshiko Ono, Mishima-gun (JP); Kayo Saito, Mishima-gun (JP); Norifumi Tateishi, Mishima-gun (JP); Akifumi Maeda, Mishima-gun (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/531,192

(22) PCT Filed: Mar. 12, 2008

(86) PCT No.: PCT/JP2008/054466
§ 371 (c)(1),
(2), (4) Date: Sep. 14, 2009

(87) PCT Pub. No.: WO2008/126587
PCT Pub. Date: Oct. 23, 2008

(65) Prior Publication Data
US 2010/0048695 A1    Feb. 25, 2010

(30) Foreign Application Priority Data
Mar. 15, 2007  (JP) ................................. 2007-067240

(51) Int. Cl.
| | | |
|---|---|---|
| *A23K 20/111* | (2016.01) | |
| *A61K 31/36* | (2006.01) | |
| *A61K 36/185* | (2006.01) | |
| *C07D 493/04* | (2006.01) | |
| *A23L 33/00* | (2016.01) | |
| *A23L 33/10* | (2016.01) | |
| *A23L 33/105* | (2016.01) | |

(52) U.S. Cl.
CPC ............. *A23K 20/111* (2016.05); *A23L 33/10* (2016.08); *A23L 33/105* (2016.08); *A23L 33/40* (2016.08); *A61K 31/36* (2013.01); *A61K 36/185* (2013.01); *C07D 493/04* (2013.01)

(58) Field of Classification Search
CPC ......... A23K 20/111; A23L 1/296; A23L 1/30; A23L 1/3002; A23L 33/10; A23L 33/105; A23L 33/40; A61K 31/36; A61K 36/185; C07D 493/04

See application file for complete search history.

(56) References Cited

U.S. PATENT DOCUMENTS

| | | | |
|---|---|---|---|
| 4,427,694 A | 1/1984 | Benecke et al. | |
| 4,496,548 A * | 1/1985 | Moldowan | A61K 31/70 514/27 |
| 5,180,588 A | 1/1993 | Shinmen et al. | |
| 5,211,953 A | 5/1993 | Shinmen et al. | |
| 5,637,610 A | 6/1997 | Nakabayashi et al. | |
| 5,814,632 A | 9/1998 | Araki et al. | |
| 5,945,420 A | 8/1999 | Araki et al. | |
| 5,948,451 A | 9/1999 | Igarashi | |
| 5,993,795 A | 11/1999 | Osawa et al. | |
| 6,159,507 A | 12/2000 | Igarashi | |
| 6,172,106 B1 | 1/2001 | Forse et al. | |
| 2002/0039599 A1 | 4/2002 | Lin et al. | |
| 2002/0198177 A1* | 12/2002 | Horrobin | A23L 1/3008 514/78 |
| 2004/0033252 A1* | 2/2004 | Yamamoto et al. | 424/439 |
| 2004/0059110 A1 | 3/2004 | Nakano et al. | |
| 2005/0158424 A1 | 7/2005 | Nakano et al. | |
| 2005/0256031 A1 | 11/2005 | Hageman et al. | |
| 2006/0058376 A1 | 3/2006 | Moritani et al. | |
| 2006/0115556 A1 | 6/2006 | Foulger et al. | |
| 2008/0020033 A1 | 1/2008 | Kawashima et al. | |
| 2009/0054443 A1 | 2/2009 | Takemoto et al. | |
| 2009/0092733 A1 | 4/2009 | Nakai et al. | |
| 2009/0169682 A1 | 7/2009 | Okumura et al. | |
| 2010/0048695 A1 | 2/2010 | Ono et al. | |

FOREIGN PATENT DOCUMENTS

| | | |
|---|---|---|
| CN | 1 836 555 A | 9/2006 |
| EP | 0524796 A1 | 1/1993 |
| EP | 0627213 A1 | 12/1994 |
| EP | 2 090 302 A1 | 8/2009 |
| EP | 2135606 A1 | 12/2009 |
| JP | 03-053866 A | 3/1991 |

(Continued)

OTHER PUBLICATIONS

Puri BK. Long-chain polyunsaturated fatty acids and the pathophysiology of myalgic encephalomyellitis (chronic fatigue syndrome). J Clin Pathol 2007; 60: 122-24.*

Ide et. al., JARQ, 2003, Japan International Research Center for Agricultural Sciences, vol. 37(3), pp. 151-158.*

Fukuda et al. "Recent Studies on Sesame Seed and Oil," *Nippon Shokuhin Kogyo Gakkaishi*, vol. 35, No. 8, 1988, pp. 552-562.

Hiramoto et al. "Sanka Stress to Hiro," *Journal of Clinical and Experimental Medicine*, Feb. 2003, vol. 204, No. 5, pp. 309-313.

Kataoka, "Sanka Stress to No no Hiro," *Journal of Clinical and Experimental Medicine*, Feb. 2003, vol. 204, No. 5, pp. 314-318.

Singh et al. "Role of Antioxidants in Chronic Fatigue Syndrome in Mice," *Indian Journal of Experimental Biology*, Nov. 2002, vol. 40, No. 11, pp. 1240-1244.

(Continued)

*Primary Examiner* — Sarah Pihonak
(74) *Attorney, Agent, or Firm* — Drinker Biddle & Reath LLP

(57) ABSTRACT

Anti-fatigue agents containing dioxabicyclo[3.3.0]octane derivatives such as sesamin which is an ingredient contained in sesame, as well as pharmaceutical compositions and physiologically functional foods that contain such anti-fatigue agents are disclosed. These compounds can safely be administered to humans and animals alike and hence allow for continued ingestion while proving effective in promoting an improvement of stamina, an increase of body strength, a relief of fatigue, and recovery from fatigue.

9 Claims, 3 Drawing Sheets

(56) References Cited

FOREIGN PATENT DOCUMENTS

| JP | 4-9331 A | 1/1992 | | |
|---|---|---|---|---|
| JP | 4-278067 A | 10/1992 | | |
| JP | 5-51388 | 3/1993 | | |
| JP | 05-058902 | 3/1993 | | |
| JP | H05-051388 A | 3/1993 | | |
| JP | 5-201864 A | 8/1993 | | |
| JP | 5194244 A | 8/1993 | | |
| JP | 6-227977 | 8/1994 | | |
| JP | 6-327435 | 11/1994 | | |
| JP | 07059540 | 3/1995 | | |
| JP | 8-26987 | 1/1996 | | |
| JP | 8-47381 | 2/1996 | | |
| JP | 9-124473 | 5/1997 | | |
| JP | 10-029941 A | 2/1998 | | |
| JP | H10218785 A | 8/1998 | | |
| JP | 2000-004832 A | 1/2000 | | |
| JP | 2001-46021 | 2/2001 | | |
| JP | 2001-139579 | 5/2001 | | |
| JP | 2003146844 A | 5/2003 | | |
| JP | 2003-183172 A | 7/2003 | | |
| JP | 2004189619 A | 7/2004 | | |
| JP | 2004-345988 | * | 12/2004 | |
| JP | 2005-023008 A | 1/2005 | | |
| JP | 2007-008878 A | 1/2007 | | |
| JP | WO 2007004570 A1 | * | 1/2007 | ........... A23L 1/3002 |
| JP | 2008-136391 A | 6/2008 | | |
| JP | 2008-285463 | 11/2008 | | |
| KR | 2001-0029185 A | 4/2001 | | |
| KR | 2002-0090077 A | 11/2002 | | |
| WO | 97-01968 A1 | 1/1997 | | |
| WO | WO-03045372 A1 | 6/2003 | | |
| WO | 2004110175 A1 | 12/2004 | | |
| WO | 2005-054415 A1 | 6/2005 | | |
| WO | WO 2007/004570 | * | 1/2007 | |
| WO | 2007-043656 A1 | 4/2007 | | |
| WO | 2007-105757 A1 | 9/2007 | | |
| WO | 2007-119378 A1 | 10/2007 | | |
| WO | 2008/007728 | 1/2008 | | |
| WO | 2008-062559 A1 | 5/2008 | | |
| WO | 2008-126587 A1 | 10/2008 | | |

OTHER PUBLICATIONS

Inoue et al. "Hirou no Kagaku (Science on Fatigue)," published by Kodansha on May 20, 2001, pp. 222-228.
Kodama et al. "The Value of the Dehydroepiandrosterone-Annexed Vitamin C Infusion Treatment in the Clinical Control of Chronic Fatigue Syndrome (CFS). II. Characterization of CFS Patients with Special Reference to their Response to a New Vitamin C Infusion Treatment," In Vivo, Nov.-Dec. 1996, vol. 10, No. 6, pp. 585-596.
International Search Report mailed Jun. 17, 2008 in International PCT Application PCT/JP2008/054466 filed Mar. 12, 2008.
Zhou et al., "Magic Sesamin," *Anhui Science & Technology*, No. 9, p. 48 (2003) (in Chinese with partial English translation).
Cu I Yun-shan, et al., "Pharmacological study on anti-aging effects of Seam in Powders", *Journal of Jilin University*, vol. 31, No. 3, May 2005, pp. 411-413 and 419 (partial English translation).
Patent Examination Report No. 2 issued Aug. 6, 2013, by the Australian Government in Australian Patent Application No. 2006239318.
Mohammad Akmal Khan, "Hab Hindi," Qaraabaadeen Azam wa Akmal (20th century AD), Matba Siddiqi, Delhi / Matba Mustafai, Delhi, 1909. (TKDL Abstract No. BA3/502).
P.V. Sharma (e.d.), "Tila Taila Prayoga," Sodhalanighantauh—(Namasamgraha Va Gunasamgraha), Oriental Institute, Baroda, 1st. Edition, 1978. (TKDL Abstract No. RG9/584B).
Therayar Kappiyam (e.d.), "Ellu Gunam", Dr. Anandakumar, Chennai, 1975. (TKDL ABstract No. SR06/116A).
P.V. Sharma (e.d.), "Tilagunah," Dhanvantarinighantauh, Chaukhambha Orientalia, Varanasi, 3rd edition, 2002. (TKDL Abstract No. AK12/482).
Therayar Maba Karisal (e.d.), "Ellu Karpam," Dr. R. Thiyagarajan, Pandit S.S. Anandam Anbu Selvi Pres. Chennai, 1974. (TKDL Abstract No. GP04/135S).
Keenoy et al., "Antioxidant status and lipoprotein peroxidation in chronic fatigue syndrome," Life Sciences 68 (2001), pp. 2037-2049.
International Search Report mailed Dec. 16, 2008 in International Application No. PCT/JP2008/066772 filed Sep. 17, 2008.
El-Arab et al., "Vitamin B1 profile of the Egyptian core foods and adequacy of intake", Food Compos. Anal 17, pp. 81-97, (2004).
Moriura et al., "Pharmacological Study on Agkistrodon blomhoffii blomhoffii BOIE. V.1) Anti-fatigue Effect of the 50% Ethanol Extract in Acute Weight-Loaded Forced Swimming-Treated Rats", Biol. Pharm. Bull. 19(1), pp. 62-66, (1996).
Ide et al., "Interaction of dietary fat types and sesamin on hepatic fatty acid oxidation in rats", Biochim. Biophys. Acta. 1682, pp. 80-91, (2004).
Webpage of http://www.doh.gov/tw/ufile/doc/A00083 (published Oct. 3, 2006) (with English translation).
Webpage of http://pure17go.youthwant.com/tw/item_id9987.htm (published Apr. 15, 2000) (with English translation).
Puri, "The use of eicosapentaenoic acid in the treatment of chronic fatigue syndrome", Prostaglandins, Leukotrienes and Essential 70, pp. 399-401 (2004).
Liu et al., "Determination of Fatty Acid Levels in Erythrocyte Membranes of Patients with Chronic Fatigue Syndrome", Nutr Neurosci 9 (6), pp. 389-392 (2003).
Life Extention. Datasheet [online]. LEM, last modified Oct. 30, 2005 [retrieved on May 14, 2013]. Retrieved from the Internet: <URL: <http://supple.s166.xrea.com/pukiwiki/index.php?cmd=read&page=LEM>.
Life Extension Vitamins. Datasheet [online]. Wayback Machine, published Feb. 9, 2006 [retrieved May 15, 2013]. Retrieved from the Internet: <URL: <http://web.archive.org/web/20060209001438/http://www.lifeextensionvitamins.com/liexmixtawex1.html>.
Chronic Fatigue Syndrome. Datasheet [online]. Wayback Machine, published Sep. 8, 2004, [retrieved May 15, 2013]. Retrieved from the Internet: <URL: <http://web.archive.org/web/20040908225030/http://lifeextensionvitamins.com/chfasysu.html>.
Duhoon et al., "Medicinal and Curative Properties of Sesame (*Sesamum indicum* L.)," J. Econ. Taxon. Bot. vol. 27, No. 1 (2003), pp. 20-28.
Supplemental European Search Report mailed Apr. 18, 2012, in EP application No. 07738720.7.
Sesame (Sesamin), http://www1.u-netsurf.ne.jp/~g-time/health/health_2-1.html, Nov. 3, 2005, and an excerpted English translation thereof (cited in the Japanese Official Action dated Sep. 18, 2012).
Hemalatha et al., "Lignans and Tocopherols in Indian Sesame Cultivars", JAOCS 81(5), pp. 467-470 (May 2004).
Shoichi et al., JP63-044843A, published Feb. 25, 1988, Machine Translation used for the Office Action.
França et al., "B vitamins induce an antinociceptive effect in the acetic acid and formaldehyde models of nociception in mice," Eur. J. Pharmacol. 421: 157-64 (2001).
Schoenen et al., "Effectiveness of high-dose riboflavin in migraine prophylaxis," Neurology 50: 466-70 (1998).
Granados-Soto et al., "Riboflavin reduces hyperalgesia and inflammation but not tactile allodynia in the rat," Eur. J. Pharmacol. 492: 35-40 (2004).
International Search Report dated Apr. 17, 2007, in PCT International Application No. PCT/JP2007/055270, filed Mar. 15, 2007.
Extended European Search Report for Application No. EP 08721882.2, dated May 15, 2014.
Nishibe et al., "Phenolic Compounds from Stem Bark of Acanthopanax senticosus and Their Pharmacological Effect in Chronic Swimming Stressed Rats", Chemical and Pharmaceutical Bulletin, Pharmaceutical Society of Japan, vol. 38, No. 6, (Jan. 1, 1990) pp. 1763-1765.
Sodhala, "Tial Taila Prayoga", TKDL, P.V. Sharma, Oriental Institute, Baroda, (Jan. 1, 1978).
Singh et al., "Effect of Natural and Synthetic Antioxidants in a Mouse Model of Chronic Fatigue Syndrome", Journal of Medicinal Food, vol. 5, No. 4, (Dec. 1, 2002), pp. 211-220.

(56) References Cited

OTHER PUBLICATIONS

Logan et al., "Chronic fatigue syndrome: oxidative stress and dietary modifications", Alternative Medicine Review, vol. 6, No. 5, (Oct. 1, 2001), pp. 450-459.

Han et al., "Studies on the Antioxidant Components of Korean Ginseng (IV)—Antifatigue Active Components -", Yakhakhoe-Chi / Taehan Yakhakhoe, Korean Intellectual Property Office, vol. 28, No. 4, (Aug. 30, 1984), pp. 231-235.

Ikeda et al., "Protective effect of sesamin administration on exercise-induced lipid peroxidation.", International Journal of Sports Medicine, vol. 24, No. 7, (Oct. 2003), pp. 530-534.

Kiso et al., "Antioxidative effects of sesamin during high intensity exercise", Medicine and Science in Sports and Exercise, vol. 35, No. 5 Supplement, 1489, (May 2003), p. S269, and at the 50th Annual Meeting of The American College of Sports Medicine; San Francisco, CA, USA; (May 28-31, 2003).

Japanese Application No. 2014-114790—Office Action mailed Jan. 5, 2016 (with partial English translation).

Cho-ri kagaku, cookery Science, 1987, vol. 20, No. 1, pp. 9-19 (with partial English translation).

International Search Report mailed Dec, 16, 2008 in International Application No. PCT/JP2008/066767 filed Sep. 17, 2008.

Extended European Search Report in European Application No. 08832483.5 mailed Sep. 13, 2010.

Suja, et al., "Free Radical Scavenging Behavior of Antioxidant Compounds of Sesame (*Sesamum indicum* L.) in DPPH System", J. Agric. Food Chem., 2004, vol. 52, pp. 912-915.

Wu, et al., "Effects of L-Malate on Physical Stamina and Activities of Enzymes Related to the Malate-Aspartate Shuttle in Liver of Mice", Physiol. Res., 2007, 56, pp. 213-220.

European Search Report in EP Application 14184312.8, issued Dec. 23, 2014.

Office Action issued Apr. 18, 2016 in European Patent Application No. 08 721 882.2.

\* cited by examiner

ANTI-FATIGUE AGENT

CROSS REFERENCE TO RELATED APPLICATIONS

This application is the National Stage of International Application No. PCT/JP2008/054466, filed Mar. 12, 2008, and claims benefit of Japanese Application No. 2007-067240, filed Mar. 15, 2007, which is incorporated herein in its entirety.

TECHNICAL FIELD

The present invention relates to anti-fatigue agents containing as the active ingredient dioxabicyclo[3.3.0]octane derivatives such as sesamin that are represented by the following general formula (I)

[Chemical Formula 1]

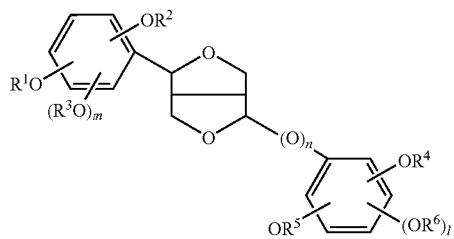

(where $R^1$, $R^2$, $R^3$, $R^4$, $R^5$ and $R^6$ each independently represent a hydrogen atom, an alkyl group having 1-3 carbon atoms, or $R^1$ and $R^2$ and/or $R^4$ and $R^5$, when taken together, represent a methylene group or an ethylene group, and n, m, and l represent 0 or 1), as well as pharmaceutical compositions (including physiologically functional foods) having an anti-fatigue action.

BACKGROUND ART

Fatigue is a disease that generally involves feelings of weariness (tiredness) and malaise (lassitude) as main symptoms but which is also accompanied by varied other symptoms including sleep disorder and lowered motivation. Feelings of weariness (tiredness) and malaise (lassitude) are one of the important alarm signals for a certain abnormality in the body and even healthy persons may perceive fatigue if they take heavy exercise, work for a prolonged period, or when they are given extreme stress. Such physiological fatigue is usually restored to the initial normal state by rest and will not last for long. According to "A Survey on Public Perception of Health" conducted by the Prime Minister's Office in 1985, about 60% plus of the people surveyed complained of fatigue but 70% of those who complained of fatigue said that "their fatigue was restored by a night's sleep." However, modern people are in many cases forced to work for a prolonged period of time or given extreme stress and yet hey have difficulty taking enough rest, so they frequency find it difficult to recover from feelings of weariness (tiredness) or malaise (lassitude). According to the epidemiological research conducted by the fatigue survey study group of the Health and Welfare Ministry in 1999, the proportion of the people who perceived fatigue remained unchanged and accounted for about 60% but then as much as 60% of those people were reported to have felt tired for more than six months. Thus, in the past 14 years, more people have become afflicted with chronic fatigue, indicating a change in the nature of fatigue (Non-Patent Document 1).

A very recent topic related to fatigue is chronic fatigue syndrome (CFS) which is considered to be one of intractable disorders. In Europe and the U.S., the first onset of this disorder was reported almost 20 years ago but here in Japan it was not until about 1991 that a fact-finding survey was launched by a dedicated study group of the Health and Welfare Ministry. General symptoms of chronic fatigue syndrome include systemic feelings of weariness (tiredness) and malaise (lassitude), slight fever, lymph node dilation, muscle pain, joint pain, and psychoneurotic symptoms, all being so prolonged as to potentially interfere with the daily life of the affected individual. Another topic of the day is "death by overwork" which presents itself as a big social problem. Death by overwork is defined as a sudden death due to prolonged overloaded work. The problem of death by overwork is recognized to be of extreme importance from medical, economic and social viewpoints.

Under these circumstances, so-called "anti-fatigue substances" have been proposed, such as those which are capable of relieving the fatigue that is experienced after taking heavy exercise, working for a prolonged time, or being given excessive stress, and those which are capable of recovery from fatigue to the normal state. For example, certain kinds of amino acid compositions (Patent Document 1), L-carnitine and histidine-related dipeptides (Patent Document 2), hawthorn extracts (Patent Document 3) and the like have been reported to have a body strength increasing action. In addition, nutrition support compositions containing ascorbic acid have been shown to be useful for the purpose of furnishing nutrition when one has lost their bodily strength due, for example, to exercise or at such times that one is tired (Patent Document 4).

The above-mentioned ascorbic acid is also known to be effective in symptomatic therapy for treating chronic fatigue syndrome (Non-Patent Document 2), and it has also been suggested that acetyl-L-carnitine is effective in the treatment of chronic fatigue syndrome (Patent Document 5).

As regards sesamin and/or episesamin, the Assignee of the subject application has shown that they have an autonomic nerve regulating action (Patent Document 6). They are also shown to have an action for alleviating the symptoms of withdrawal from alcohol or tobacco intoxication (Patent Document 7). However, none of these documents suggest or disclose the anti-fatigue action.

[Patent Document 1] Official Gazette of JP 9-124473 A
[Patent Document 2] Official Gazette of JP 2001-046021 A
[Patent Document 3] Official Gazette of JP 8-47381 A
[Patent Document 4] Official Gazette of JP 6-327435 A
[Patent Document 5] Official Gazette of JP 8-26987 A
[Patent Document 6] International Publication WO 2004-105749
[Patent Document 7] Official Gazette of U.S. Pat. No. 4,427,694
[Non-Patent Document 1] M. Inoue et al. "Hirou no Kagaku (Science on Fatigue)" published by Kodansha on May 20, 2001, p. 222-228
[Non-Patent Document 2] In Vivo (1996) November-December; 10(6):585-96

DISCLOSURE OF THE INVENTION

Problem to be Solved by the Invention

An object of the present invention is to provide compositions, in particular, pharmaceutical compositions that are safe to humans and animals alike and which therefore allow for continued ingestion while proving effective in preventing and/or treating fatigue.

Means for Solving the Problem

The present inventors conducted intensive studies with a view to solving the above-mentioned problem; as a result, they found that dioxabicyclo[3.3.0]octane derivatives such as sesamin which is an ingredient in sesame have the activity of promoting an improvement of stamina, an increase in body strength, a relief of fatigue, and recovery from fatigue; the present invention has been accomplished on the basis of this finding.

Thus, the present invention relates to the following:
1. An anti-fatigue agent containing as the active ingredient a dioxabicyclo[3.3.0]octane derivative such as sesamin that is represented by the following general formula (I)

[Chemical Formula 2]

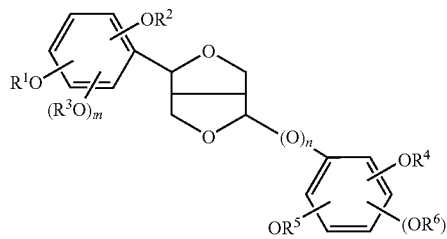

(I)

(where $R^1$, $R^2$, $R^3$, $R^4$, $R^5$ and $R^6$ each independently represent a hydrogen atom, an alkyl group having 1-3 carbon atoms, or $R^1$ and $R^2$ and/or $R^4$ and $R^5$, when taken together, represent a methylene group or an ethylene group, and n, m, and l represent 0 or 1).
2. The anti-fatigue agent according to 1 above, wherein the dioxabicyclo[3.3.0]octane derivative is sesamin.
3. A pharmaceutical composition containing the anti-fatigue agent according to 1 or 2 above, for treating or preventing a disorder that involves fatigue.
4. The pharmaceutical composition according to 3 above, wherein the disorder that involves fatigue is chronic fatigue syndrome.
5. Use of the dioxabicyclo[3.3.0]octane derivative according to 1 above, for recovery from fatigue or prevention of fatigue.
6. The use according to 5 above, wherein the dioxabicyclo [3.3.0]octane derivative is sesamin.
7. The use according to 5 or 6 above, for treating or preventing a disorder that involves fatigue.
8. The use according to 7 above, wherein the disorder that involves fatigue is chronic fatigue syndrome.

Advantages of the Invention

The anti-fatigue agents of the present invention have an outstanding action for promoting an improvement of stamina, an increase in body strength, a relief of fatigue, and recovery from fatigue and, what is more, they can be safely administered to humans and animals alike and hence allow for continued ingestion. Therefore, the anti-fatigue agents of the present invention are widely applicable as pharmaceutical compositions including physiologically functional foods.

Figure 1:
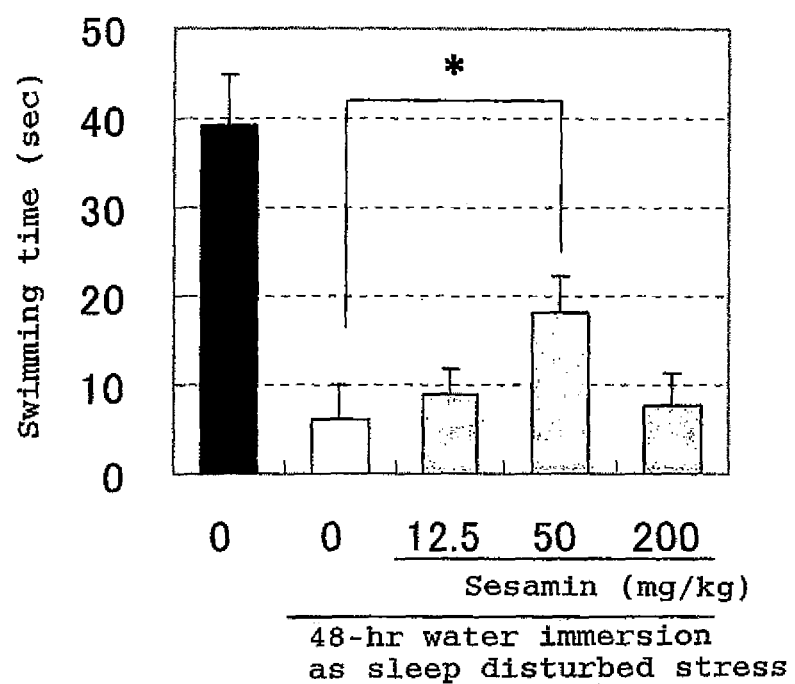
FIG. 1 is a graph showing how the administration of sesamin was effective for controlling the shortening of the swimming time (for relieving fatigue) in a forced swimming test under load.

BEST MODE FOR CARRYING OUT THE INVENTION (Dioxabicyclo[3.3.0]Octane Derivatives)

Examples of the dioxabicyclo[3.3.0]octane derivatives that may be used in the present invention include sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane, 2-(3,4-methylenedioxyphenyl)-6-(3-methoxy-4-hydroxyphenoxy)-3,7-dioxabicyclo[3.3.0]octane, 2-(3-methoxy-4-hydroxyphenyl)-6-(3,4-dihydroxyphenyl)-3,7-dioxabicyclo [3.3.0]octane, 2,6-bis(3,4-dihydroxyphenyl)-3,7-dioxabicyclo[3.3.0]octane, 2-(3,4-methylenedioxyphenyl)-6-(3,4-dihydroxyphenyl)-3,7-dioxabicyclo[3.3.0]octane, etc. These stereoisomers or racemates may be used either alone or in admixture, and among others, sesamin may be used with advantage.

Sesamin as used herein shall mean sesamin and/or episesamin. In addition, the metabolites of sesamin that are described in the official gazette of JP 2001-139579 A may, as long as they exhibit the effects of the present invention, be classified as the dioxabicyclo[3.3.0]octane derivatives of the present invention and can be used in the present invention. Those compounds which are to be used in the present invention and extracts that contain those compounds as main ingredients can be obtained by known methods such as the one described in Japanese Patent No. 3075358.

The compounds to be used in the present invention are either compounds that have been discovered in existing foods or their analogous compounds, so they obviously have another advantage of outstanding safety. This is demonstrated by the fact that 7-week old ICR male mice were continuously administered 2.14 g/day/kg of sesamin for two weeks (by oral route), with no abnormal symptoms being recognized.

(Anti-Fatigue Action and Agent)

Ingesting the above-mentioned sesamin or other dioxabicyclo[3.3.0]octane derivatives helps provide a marked anti-fatigue action. Fatigue as appears here is a temporary lowering of physical or mental performance that results from continued application of a physical or mental stress and lowered performance means a drop in the quality or quantity of a physical or mental working capacity. It should also be noted that the term "fatigue" as used herein covers chronic fatigue syndrome and death by overwork.

The "anti-fatigue action" as used herein, namely, the effect of the "anti-fatigue agent" refers to its action for attenuating the above-defined fatigue or achieving recovery from it and includes the following effects: prolonging the duration for which a moving or acting site (including the brain) keeps functioning, and controlling the increase in fatigue-causing substances given the same amount of motion or action (improvement of stamina and increase of body strength); or ameliorating such a condition that the brain or nerves have come to perceive fatigue although a moving or acting site is yet to get tired, and promoting the recovery of the moving or acting site from the tired state to the normal state.

Chronic fatigue syndrome which is to be treated with the anti-fatigue agent of the present invention means general symptoms such as systemic feelings of weariness (tiredness) and malaise (lassitude), slight fever, lymph node dilation, muscle pain, joint pain, and psychoneurotic symptoms, all being so prolonged as to potentially interfere with the daily life of the affected individual. The anti-fatigue agent of the present invention is capable of treating chronic fatigue syndrome; in other words, it can palliate the various symptoms of chronic fatigue syndrome such that the affected individual is brought to the normal condition. Death by overwork which is also to be treated with the anti-fatigue agent of the present invention means such a condition of individuals who are under extreme fatigue and unable to keep physical vigor that they are no longer capable of fully perceiving fatigue, with the result that cardiovascular disease or cardiac disease manifests itself, causing the individuals to become permanently unable to work or bringing them to death. The anti-fatigue agent of the present invention is capable of treating chronic fatigue syndrome, whereby it can prevent death from overwork.

The effectiveness of the "anti-fatigue agent" of the present invention can be verified by the following tests.

The first thing to do is measure the swimming time in a water immersion sleep disturbed test. Mice that have been kept in an environment such as water immersion where they are unable to have a good sleep or take a rest position so they cannot have a physical or mental rest are forced to swim under a weight load and the time it takes for them to have their nose sunk in the water for a period of ten seconds or longer is measured to confirm the degree of their fatigue. Since this is an animal model for physical or mental fatigue, an extension of the swimming time as achieved by administering it with the test substance means the verification of resistance to fatigue, as exemplified by relief of physical and/or mental fatigue, maintenance of physical vigor in the tired model (increase in body strength), or improvement of stamina.

The second thing to do is measure the motor activity in a forced exercise test. Rats administered with the test substance are forced to have exercise on a treadmill and, thereafter, the motor activity of the animal in the dark period is measured. Since this is an animal model for fatigue from exercise (physical fatigue), an increase in the motor activity as achieved by administering it with the test substance means the verification of resistance to fatigue.

The third thing to do is measure the amount of fatigue-causing substances in the blood. This involves administering the test substance to check to see if it has an action for controlling an increase in the blood concentration of fatigue-causing substances under a physical or mental stress. Although no substances have been identified to be causative of fatigue, one class of candidates may be ketone bodies (collectively referring to acetoacetate, 3-hydroxybutyrate, and acetone). Ketone bodies are known to be metabolites that are produced when free fatty acids immobilized from the fat tissue on account of lowered glucose availability undergo β-oxidation. If the production of ketone bodies is enhanced beyond their utilization in the extrahepatic tissues, ketone bodies accumulate in the blood, leading to ketosis. Actoacetate and 3-hydroxybutyrate are moderately strong acids, so if ketone bodies accumulate in amounts exceeding the buffering action of the living body, the blood becomes acidic, causing a condition known as acidosis which, in turn, produces a feeling of weariness (Takanori Yamamoto, Igaku no ayumi (Progress in Medicine), Vol. 204, No. 5:325-329, 2003).

Sesamin used as a dioxabicyclo[3.3.0]octane derivative has been verified to have a fatigue-resisting effect in each of the above-described tests for anti-fatigue action, namely, in the water immersion sleep disturbed test, forced exercise test, and the measurement of the amount of fatigue-causing substances. This means sesamin is useful not only as an anti-fatigue agent but also in preventing or treating chronic fatigue syndrome, and in preventing death from overwork. Since sesamin also controls an increase in fatigue-causing substances in the blood (ketone bodies), it may well be said that sesamin is also useful as an agent for ameliorating ketosis. Alanine, aspartic acid, and glutamine have been reported to be effective in reducing blood ketone levels in the living body (Romano Nosadini, Biochem. J., 190, 323-332, 1980; Eugenio Cersosimo, Am. J. Physiol., 250, E248-E252, 1986); however, the effect of these amino acids for lowering ketone bodies is only transient if they are administered in a single dose and because of this short duration of their efficacy, single doses of these amino acids have to be administered frequently in order to ameliorate ketosis. In contrast, a ketosis ameliorating agent containing the dioxabicyclo[3.3.0]octane derivative such as sesamin of the present invention was shown to have an action for reducing the levels of ketone bodies when it was ingested for two consecutive days on a single-dose-a-day basis (see Example 4) and this ease of ingestion may also explain the superiority of this ketosis ameliorating agent.

As described above, the anti-fatigue agent of the present invention has such an effect that if one ingests it, he or she will not get tired easily and, if tired, may soon recover from the fatigue. In other words, if one perceives physical fatigue as a result of taking a muscular exercise such as sport or if one perceives mental fatigue as a result of a continued work such as a calculating operation, he or she may of course ingest the anti-fatigue agent of the present invention with a view to recovering from the fatigue; if desired, one may ingest the anti-fatigue agent of the present invention and then start working or doing sport, without perceiving much fatigue (the fatigue preventing effect). Ingesting it before one does sport or while one is doing sport, his or her stamina is likely to be improved. What is more, if it is ingested on a regular basis, not only mental fatigue but also some disorder that accompanies it can be prevented.

The anti-fatigue agent of the present invention can be used as a pharmaceutical drug or as food (i.e., one that may be administered perorally, as exemplified by physiologically functional foods, health supplements, foods with nutrient function claims, foods for special uses, and foods for specified health use). The anti-fatigue agent of the present invention may be used in such a way that the type of the active ingredient, the use for which the agent is indicated, its efficacy such as improved stamina or anti-fatigue effect, and/or the method of ingestion is identified on the package, container, or manual.

If the anti-fatigue agent of the present invention is to be used as a pharmaceutical drug, the dioxabicyclo[3.3.0]octane derivatives may be used either alone or together with a pharmacologically acceptable carrier, diluent, excipient or the like, for oral administration in the form of a liquid, tablet, granule, powder, capsule, dry syrup, pill or the like, or for parenteral administration in the form of an injection or the like. The dose and dosage form of the anti-fatigue agent may be chosen as appropriate for the subject to be treated, his or her pathological state, the severity of its progress, and other conditions; if sesamin is chosen as the dioxabicyclo[3.3.0] octane derivative and is to be administered perorally with a view to obtaining the anti-fatigue action in a human (adult) as the subject, then it may generally be administered continuously at a frequency of once or twice a day to give a daily dose of about 1-200 mg, preferably about 5-100 mg. The present inventors made an investigation using mice or rats as tired animal models and confirmed that when it was desired to relieve mental or physical fatigue by preliminary administration of sesamin, the intended anti-fatigue action could be obtained by administering sesamin in an amount of about 10-100 mg/kg, preferably about 10-80 mg/kg, more preferably about 12.5-80 mg/kg, and even more preferably about 50-80 mg/kg. The present inventors also confirmed that when it was desired to promote recovery from existing physical fatigue by administering sesamin, the intended anti-fatigue action could be obtained by administering sesamin in an amount of at least 100 mg/kg, preferably at least 150 mg/kg, more preferably at least 180 mg/kg.

In the case of parenteral administration, the anti-fatigue agent of the present invention may be administered by intravenous injection at a frequency of about three times a week, preferably about once in two days, to give a daily dose of about 0.1-20 mg, preferably about 0.5-10 mg.

If the anti-fatigue agent of the present invention is to be used as food, the content of the active ingredient is not limited in any particular way as long as it is capable of providing the anti-fatigue action of sesamin and it may be chosen as appropriate for the physical form of the food (e.g., capsule, tablet, or drink). Depending on the type of the dioxabicyclo[3.3.0]octane derivative used, the content of the active ingredient is typically in the range of 0.001-5 wt %, preferably 0.01-5 wt %, more preferably 0.05-5 wt %. In the case of a drink, the content of the active ingredient is preferably in the range of 0.0005-0.05 wt %, more preferably 0.002-0.01 wt %.

Insofar as the effect of the dioxabicyclo[3.3.0]octane derivative is not impaired, namely, to the extent that incorporation in the dioxabicyclo[3.3.0]octane derivative will not produce any unwanted interaction, the anti-fatigue agent of the present invention may have mixed therewith other additives such as other physiologically active ingredients, minerals, vitamins, hormones, nutritional ingredients, and flavors. All these additives may be chosen from among those which are commonly used in pharmaceuticals and foodstuffs.

The anti-fatigue agent of the present invention is effective not only in humans but also in draft animals, hunting dogs, racehorses, pet animals, and various other kinds of animals.

EXAMPLES

The present invention is described in greater detail by means of the following examples, to which the present invention is by no means limited.

Example 1

Water Immersion Sleep Disturbed Test

A sesamin/episesamin mixture (sesamin:episesamin=1:1 in weight ratio) was used as a test sample.

Effectiveness against fatigue was evaluated by the following partial modification of the method of Tanaka et al. (Neuroscience, Let. 352, 159-162, 2003). The test animals Balb/c male mice (8-week old) were divided into five groups, each consisting of 12 animals and having the same average body weight. Four of those five groups were water immersion groups, which were kept in breeding cages, not on paper chips but in tap water (23° C.) supplied to a depth of 7 mm, thereby disturbing sleep of the mice. During a two-day immersion in water, the mice were forcibly administered with the test sample sesamin orally for two days on a one-dose-a-day basis at varying doses of 12.5, 50, and 200 mg/5 ml olive oil/kg body weight (the group kept under water immersion stress and administered with sesamin). The control group mice were forcibly administered with olive oil (5 ml/kg) orally on a one-dose-a-day basis (the control group kept under water immersion stress). The remaining group was a normally kept group and the mice in this group were kept in breeding cages where conventional paper chips were laid down, and were forcibly administered with olive oil orally on a one-dose-a-day basis (the normally kept control group). After two days, each mouse was fitted with a weight at the tail which corresponded to 8% of its body weight, and was allowed to swim in a water tank of 18 cm$^\Phi$ that was filled with water to a depth of 30 cm; the time it took for each mouse to have its nose sunk in water for a period of at least 10 seconds was measured.

The mice in the groups kept under water immersion stress could swim for a shorter period than the mice in the normally kept group and the degree by which the shortening of the swimming time could be controlled in the sesamin administered groups was measured to evaluate the effectiveness of sesamin against fatigue. The results are shown in FIG. 1 (wherein the asterisk represents significant differences at a risk factor of 0.05% in a Student's t-test).

As is clear from the data shown in FIG. 1, the swimming time of the mice in the control group kept under water immersion stress was significantly shorter than that of the mice in the normally kept group. However, the shortening of the swimming time was markedly controlled in the groups kept under water immersion stress after being administered with sesamin. When the swimming time of the control group kept under water immersion stress was taken as 100%, those of the groups given sesamin were 150%, 300% and 133% at respective doses of 12.5, 50 and 200 mg/kg, indicating that the shortening of the swimming time could be effectively controlled by administering sesamin. The shortening of the swimming time was controlled most effectively when sesamin was administered in 12.5-50 mg/kg (more preferably when administered in 50 mg/kg). From these data, it is obvious that sesamin is capable of achieving recovery from fatigue by significantly relieving the fatigue that would otherwise be caused by stress under sleep disturbance from water immersion (i.e., increasing the resistance to fatigue).

Example 2

Forced Exercise Test

The test sample used in Example 2 was the same sesamin as in Example 1.

Sprague Dawley male rats (6-week old) were acclimatized in a test environment for a week and the animals that had shown normal growth were subjected to the test. One day before the start of the test, the rats were divided into five groups each consisting of eight animals. On the day of the test, all animals were starved from the morning and one group of rats was assigned as a resting group that was not to be subjected to exercise stress. The animals in the other four groups were given a 3-hr exercise stress by means of a treadmill-type forced walking apparatus (MK-680 manufactured by MUROMACHI KIKAI CO., LTD.) After the end of exercise stress application, the test sample sesamin as dissolved in olive oil (5 ml/kg) was forcibly administered orally through a feeding tube at a dose of 20, 60, or 180 mg/kg. The rats in the control group under exercise stress were forcibly administered with olive oil orally at a dose of 5 ml/kg. Thereafter, the animals were transferred to an automatograph (Supermex manufactured by MUROMACHI KIKAI CO., LTD.) and their motor activity in the dark period was measured.

Figure 2:
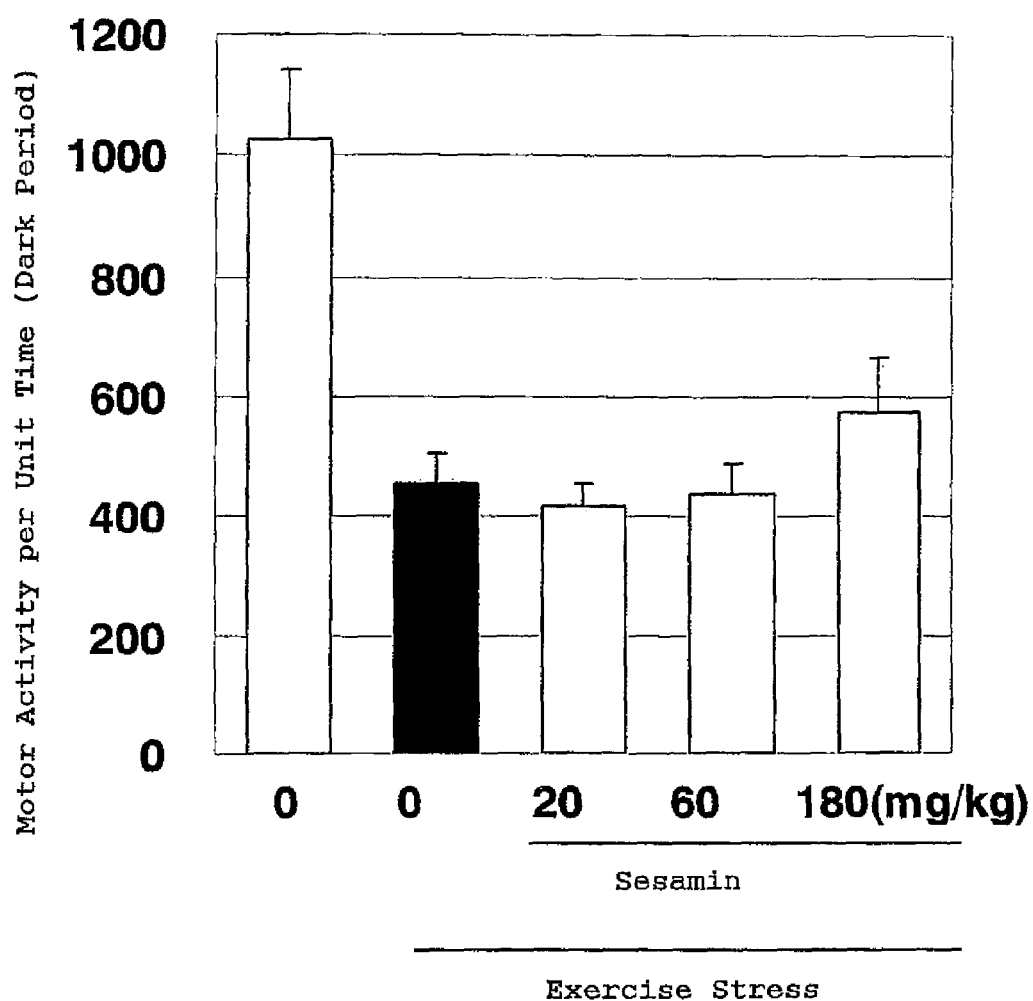
FIG. 2 is a graph showing by motor activity the degree by which rats recovered from fatigue in a forced exercise test when they were administered sesamin.

The sesamin-induced recovery of rats from the fatigue they suffered as the result of forced application of exercise stress was evaluated in terms of motor activity. The results are shown in FIG. 2. As is clear from the data in FIG. 2, the motor activity of the rats in the control group given exercise stress was considerably smaller than that of the control group under no stress. This shows that the rat under exercise stress reflects the state of fatigue. In the treated groups of those model animals, an increase in the motor activity was confirmed when sesamin was administered in 180 mg/kg. Administering sesamin was evidently capable of promoting recovery from fatigue caused by exercise.

Example 3

Forced Exercise Test

The test sample used in Example 3 was the same sesamin as in Example 1.

Sprague Dawley male rats (10-week old) were acclimatized in a test environment for a week and the animals that had shown normal growth were subjected to the test. The rats were divided into three groups each consisting of eight animals. Then, AIN93G was mixed with sesamin to give final concentrations of 0, 0.02, and 0.1% (w/w) to prepare feeds and the rats were let to ingest the respective feeds ad libitum for a week. Thereafter, all animals were given a 3-hr exercise stress by means of a treadmill-type forced walking apparatus (MK-680 manufactured by MUROMACHI KIKAI CO., LTD.) After the end of exercise stress application, the animals were transferred to an automatograph (Supermex manufactured by MUROMACHI KIKAI CO., LTD.) and their motor activity in the dark period was measured.

Figure 3:
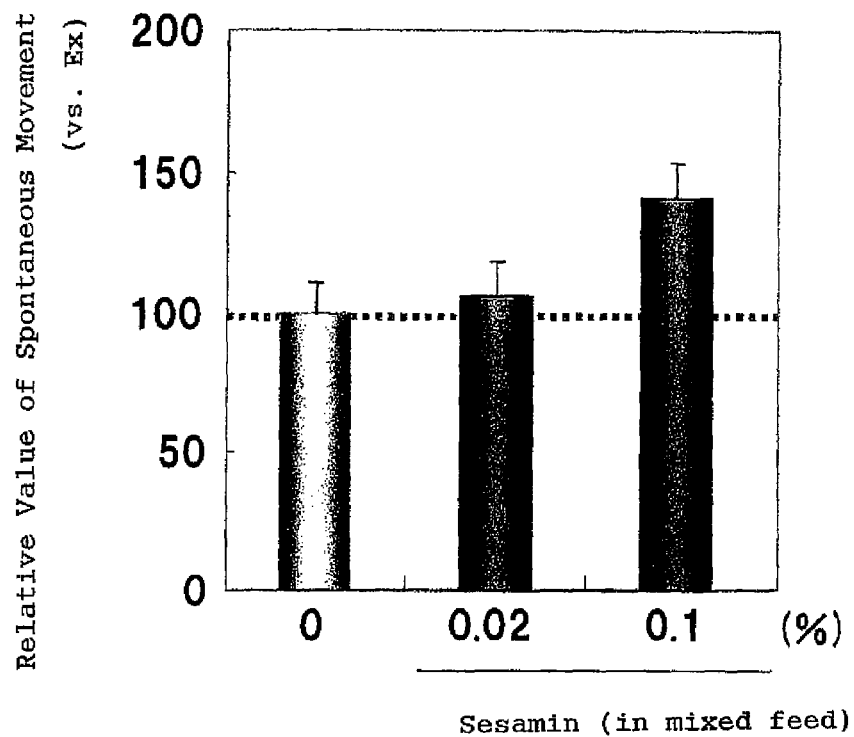
FIG. 3 is a graph showing by motor activity the degree by which rats were prevented from becoming tired in a forced exercise test when they were administered sesamin.

The purpose of the experiment conducted in Example 3 was to determine how much of the fatigue that might be caused to the rats upon forced application of exercise stress would be prevented by preliminary ingestion of sesamin and this was evaluated by measuring the motor activity of the rats. The results are shown in FIG. 3. In comparison with the exercise fatigue control group which did not ingest sesamin and the physical activity of which was taken as the reference, the group ingesting a mixed feed containing 0.02% sesamin showed almost the same physical activity whereas the group ingesting a mixed feed containing 0.1% sesamin showed an enhanced physical activity. Administering the mixed feed containing 0.1% sesamin corresponds to administering about 80 mg of sesamin per kilogram of body weight. From these data, it was clear that preliminary continued ingestion of sesamin was capable of preventing physical fatigue. What is more, preventing physical fatigue by ingesting sesamin before taking exercise was found to effective at a lower dose than in Example 2. This suggests that the effective dose of sesamin differs depending upon whether it is administered preliminarily or administered after one gets tired.

Example 4

Measuring Fatigue-Causing Substances in the Blood

The fatigue from metabolites in the living body was studied with the variation in ketone bodies being used as a marker. To check for any effect on the marker, the procedure of Example 1 was slightly modified as described below to prepare sleep-disturbed animals under stress by water immersion. The test animals Balb/c male mice (8-week old) were divided into three groups, consisting of 7-10 animals and having the same average body weight. Two of those three groups were water immersion groups, which were kept in breeding cages, not on paper chips but in tap water (23° C.) supplied to a depth of 5 mm, thereby causing the mice to be immersed in water. During a three-day immersion in water, the mice were forcibly administered with the test sample sesamin orally for three days on a one-dose-a-day basis at a dose of 50 mg/kg body weight as dissolved in olive oil in an amount of 5 ml/kg body weight (the group kept under water immersion stress and administered with sesamin). The control group mice were forcibly administered with olive oil (5 ml/kg) orally at the same frequency as the treated group (the control group kept under water immersion stress). The remaining group was a normally kept group and the mice in this group were kept in breeding cages where conventional paper chips were laid down, and were forcibly administered with olive oil (5 ml/kg) orally at the same frequency as the treated group (the normally kept control group).

After three days, blood was drawn from each mouse and the ketone bodies in the serum were measured by the enzyme method with a biochemical automatic analyzer (Model 7070 of Hitachi, Ltd.)

Figure 4:
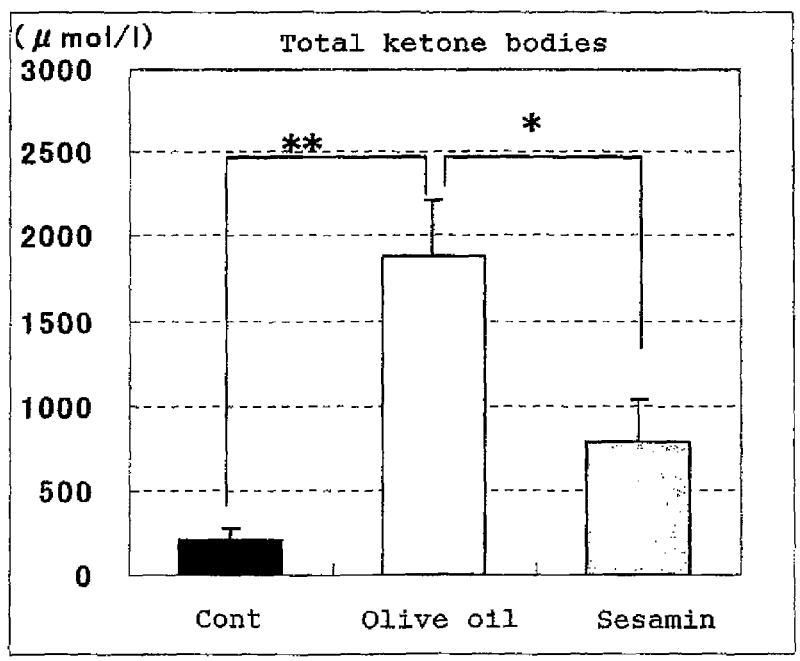
FIG. 4 is a graph showing how the administration of sesamin was effective for controlling the elevation of serum level of ketone bodies in the measurement of fatigue-causing substances in the blood.

The results of measurement of ketone bodies are shown in FIG. 4, wherein the single and double asterisks represent significant differences at risk factors of 0.05% and 0.01%, respectively, in a Student's t-test. As is clear from the data shown in FIG. 4, the concentration of ketone bodies in the sera of the mice in the control group kept under water immersion stress (Olive Oil) increased significantly compared with the mice in the normally kept control group (Cont). On the other hand, the mice in the group kept under water immersion stress and administered with sesamin (Sesamin) experienced a significant control of the increase in the concentration of ketone bodies.

The foregoing results suggest that sesamin suppresses the production of ketone bodies due to keep under water immersion stress, thereby relieving fatigue or contributing to recovery from fatigue so as to achieve effective prevention or treatment of ketosis.

The invention claimed is:

1. A method for treating a fatigue in a subject comprising administering to the subject at least one dioxabicyclo[3.3.0] octane derivative that is represented by the following general formula (I)

[Chemical Formula 1]

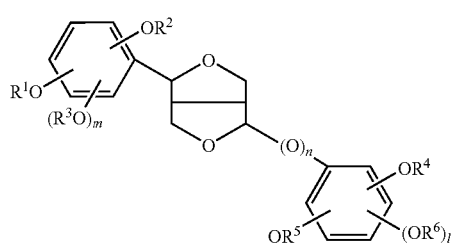

(I)

where $R^1$, $R^2$, $R^3$, $R^4$, $R^5$ and $R^6$ each independently represent a hydrogen atom, an alkyl group having 1-3 carbon atoms, or $R^1$ and $R^2$ and/or $R^4$ and $R^5$, when taken together, represent a methylene group or an ethylene group, and n, m, and l represent 0 or 1, to treat the fatigue in the subject, wherein the fatigue is mental fatigue, and wherein the dioxabicyclo[3.3.0]octane derivative is sesamin and/or episesamin, and wherein the dioxabicyclo[3.3.0]octane derivative is administered to said subject in an amount corresponding to 50 to 80 mg/kg in mice.

2. A method for reducing risk of developing a fatigue in a subject comprising administering to the subject at least one dioxabicyclo[3.3.0]octane derivative that is represented by the following general formula (I)

[Chemical Formula 1]

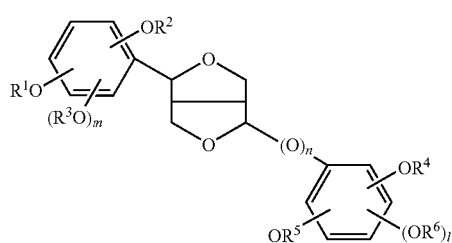

(I)

where $R^1$, $R^2$, $R^3$, $R^4$, $R^5$ and $R^6$ each independently represent a hydrogen atom, an alkyl group having 1-3 carbon atoms, or $R^1$ and $R^2$ and/or $R^4$ and $R^5$, when taken together, represent a methylene group or an ethylene group, and n, m, and l represent 0 or 1, to reduce risk of developing the fatigue in the subject, wherein the fatigue is mental fatigue, and wherein the dioxabicyclo[3.3.0]octane derivative is sesamin and/or episesamin, and wherein the dioxabicyclo[3.3.0]octane derivative is administered to the subject in an amount corresponding to 50 to 80 mg/kg in mice.

3. A method for promoting recovery from fatigue in a subject comprising administering to the subject at least one dioxabicyclo[3.3.0]octane derivative that is represented by the following general formula (I)

[Chemical Formula 1]

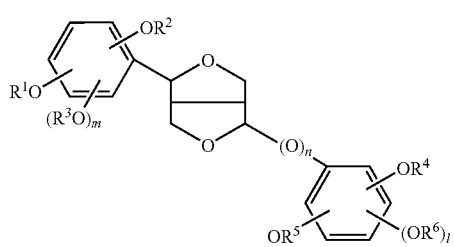

(I)

where $R^1$, $R^2$, $R^3$, $R^4$, $R^5$ and $R^6$ each independently represent a hydrogen atom, an alkyl group having 1-3 carbon atoms, or $R^1$ and $R^2$ and/or $R^4$ and $R^5$, when taken together, represent a methylene group or an ethylene group, and n, m, and l represent 0 or 1, to promote recovery from fatigue in the subject, wherein the fatigue is mental fatigue, and wherein the dioxabicyclo[3.3.0]octane derivative is sesamin and/or episesamin, and wherein the dioxabicyclo[3.3.0]octane derivative is administered to the subject in an amount corresponding to 50 to 80 mg/kg in mice.

4. A method for reducing a possibility in a subject of suffering from fatigue comprising administering to the subject at least one dioxabicyclo[3.3.0]octane derivative that is represented by the following general formula (I)

[Chemical Formula 1]

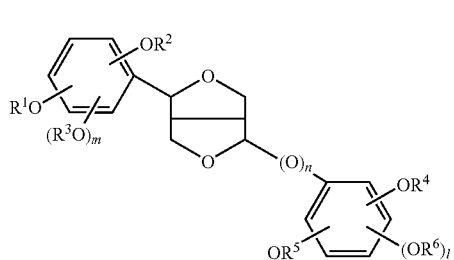

(I)

where $R^1$, $R^2$, $R^3$, $R^4$, $R^5$ and $R^6$ each independently represent a hydrogen atom, an alkyl group having 1-3 carbon atoms, or $R^1$ and $R^2$ and/or $R^4$ and $R^5$, when taken together, represent a methylene group or an ethylene group, and n, m, and l represent 0 or 1, to reduce a possibility in the subject of suffering from fatigue, wherein the fatigue is mental fatigue, and wherein the dioxabicyclo[3.3.0]octane derivative is sesamin and/or episesamin, and wherein the dioxabicyclo[3.3.0]octane derivative is administered to the subject in an amount corresponding to 50 to 80 mg/kg in mice.

5. A method for ameliorating ketosis in a subject comprising administering to the subject at least one dioxabicyclo[3.3.0]octane derivative that is represented by the following general formula (I)

[Chemical Formula 1]

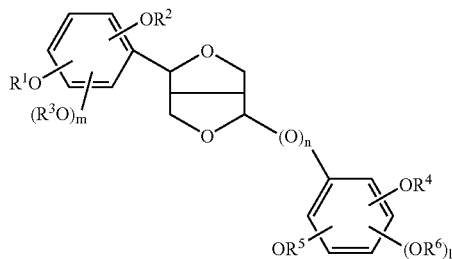

(I)

where $R^1$, $R^2$, $R^3$, $R^4$, $R^5$ and $R^6$ each independently represent a hydrogen atom, an alkyl group having 1-3 carbon atoms, or $R^1$ and $R^2$ and/or $R^4$ and $R^5$, when taken together, represent a methylene group or an ethylene group, and n, m, and l represent 0 or 1, to ameliorate ketosis in the subject, wherein the dioxabicyclo[3.3.0]octane derivative is sesamin and/or episesamin, and wherein the dioxabicyclo[3.3.0]octane derivative is administered to the subject in an amount corresponding to 50 to 80 mg/kg in mice.

6. The method according to claim 1, wherein the fatigue comprises feelings of weariness (tiredness), malaise (lassitude), a sleep disorder, or lowered motivation.

7. The method according to claim 2, wherein the fatigue comprises feelings of weariness (tiredness), malaise (lassitude), a sleep disorder, or lowered motivation.

8. The method according to claim 3, wherein the fatigue comprises feelings of weariness (tiredness), malaise (lassitude), a sleep disorder, or lowered motivation.

9. The method according to claim 4, wherein the fatigue comprises feelings of weariness (tiredness), malaise (lassitude), a sleep disorder, or lowered motivation.

* * * * *